United States Patent [19]
Broad, Jr.

[11] Patent Number: 5,425,379
[45] Date of Patent: Jun. 20, 1995

[54] ROLLING RING CONDOM

[76] Inventor: Robert L. Broad, Jr., 2300 Brookwood Dr., SE., Decatur, Ala. 35601

[21] Appl. No.: 883,684

[22] Filed: May 15, 1992

[51] Int. Cl.⁶ .............................................. A61F 6/04
[52] U.S. Cl. .................... 128/842; 128/844; 128/916
[58] Field of Search .............. 128/842, 844, 918; 604/330, 347–353

[56] References Cited

U.S. PATENT DOCUMENTS

| | | | |
|---|---|---|---|
| 2,326,159 | 8/1943 | Mendel | 604/349 |
| 2,577,345 | 12/1951 | McEwen | 128/844 |
| 2,586,674 | 2/1952 | Lönne | 604/349 |
| 2,816,542 | 12/1957 | Freeman | 128/132 |
| 4,798,600 | 1/1989 | Meadows | 128/844 |
| 4,919,149 | 4/1990 | Stang | 128/844 |
| 4,920,983 | 5/1990 | Jimenez | 604/349 |
| 4,984,582 | 1/1991 | Romaniszyn | 128/844 |
| 5,027,831 | 7/1991 | Reddy | 128/844 |
| 5,070,890 | 12/1991 | Papurt | 128/844 |
| 5,082,004 | 1/1992 | Reddy | 128/844 |
| 5,102,405 | 4/1992 | Conway | 128/844 |
| 5,111,831 | 5/1992 | Foggia | 128/842 |

Primary Examiner—Michael A. Brown

[57] ABSTRACT

A contraceptive device having a condom that has a configuration of an elongated tube having an open end and a closed end. A sheath surrounds at least a portion of the tubular condom. The sheath has an attachment end and a distal end. The attachment end of the sheath is attached to the condom at a first point. The distal end of sheath is located at a second point spaced from the first point. An elastic ring is secured to the distal end of the sheath. The sheath is unattached to the condom between the points such that the elastic ring is free to move back and forth between the points.

11 Claims, 3 Drawing Sheets

ROLLING RING CONDOM

BACKGROUND

1. Field of the Invention

This invention relates to contraceptive devices.

2. Prior Art

U.S. Pat. Nos. 5,027,831 and 5,082,004 disclose a condom having a pouch-on-pouch structure which, from the description, moves back and forth a short distance relative to the glans penis area of the penis. A disadvantage of this arrangement is that, unless there is some movement of the condom relative to the penis, there cannot be much movement of the pouch-on-pouch relative to the penis. A further disadvantage is that the pouch-on-pouch arrangement cannot supply any stimulation other than a mere rubbing action.

U.S. Pat. No. 2,816,165 discloses a condom having a thickened portion positioned to inhibit the degree of stimulation of the critical area of sensitivity in the male organ. This intended result is exactly the opposite of the result achieved with the condom of this invention.

SUMMARY OF THE INVENTION

A contraceptive device made up of a condom which has a closed end and an open end and which is surrounded by a sheath having an attachment end and a distal end, the distal end terminating in an elastic ring positioned adjacent to the closed end of the condom. The attachment end of the sheath is attached to the condom at a point spaced from the closed end, with the remainder of the sheath being unattached to the condom so that the elastic ring is free to roll back and forth along the penis from its position adjacent to the closed end of the condom to the point of attachment. During coitus the moving ring will apply both a rubbing action and a squeezing action to the penis and a rubbing or rolling action to the clitoris of the female partner to stimulate both of the partners. The distance of movement of the ring can be adjusted by moving the point of attachment of the sheath to the condom.

DETAILED DESCRIPTION OF THE INVENTION

Figure 1:
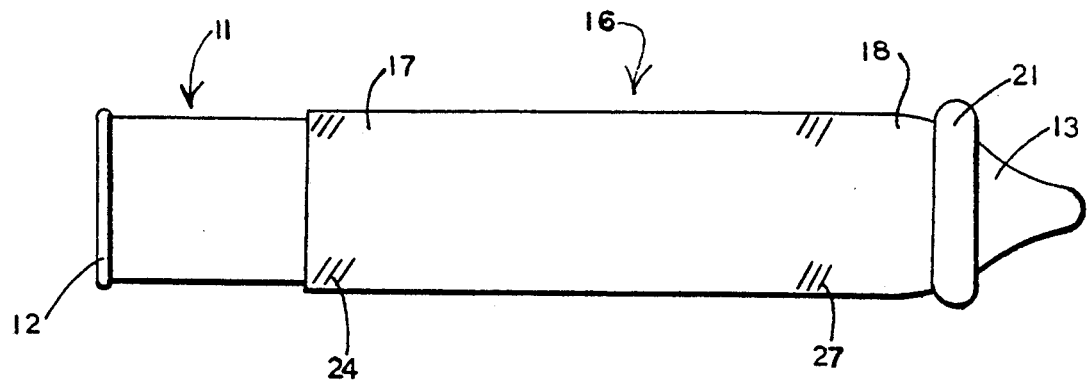
FIG. 1 is a side view of the device of this invention showing the elastic ring at one end of its distance of travel, as well as indicating where the sheath which carries the elastic ring is attached to a condom.
Figure 2:
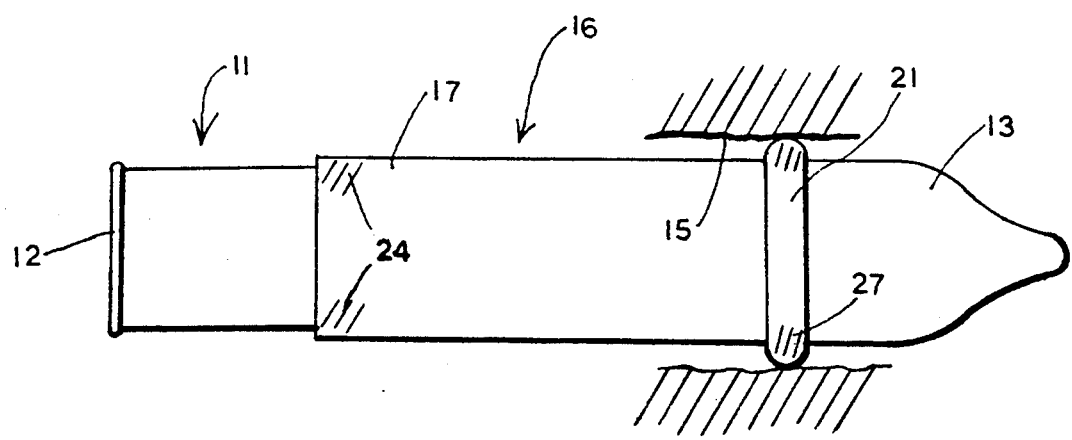
FIG. 2 is a side view showing the elastic ring at the other end of its distance of travel.

Referring now in detail to FIGS. 1 and 2 of the drawings, there is shown a contraceptive device made up of a condom 11 having an open end 12 and a closed end 13. This condom is conventional and well known. Surrounding the condom 11 is a sheath 16 having an attachment end 17 and a distal end 18, with the distal end 18 of the sheath terminating in and being secured to an elastic ring 21. In the embodiment shown the ring 21 is formed by making the sheath 16 a suitable length and then rolling one end of it to form the ring.

The sheath 16 is preferably made of the same material from which the condom 11 is made, with about the same elasticity that the condom has. Latex is a preferred material for making the sheath. The sheath 16 may be about the same in diameter as the condom 11 but is preferably about 5 to 10% smaller in diameter than the condom in order to fit snugly on the condom.

The purpose of the elastic ring is to move back and forth along the end of the condom 11 and, consequently, along the penis, during coitus. Preferably, the dimensions and elasticity of the ring 21 will be selected to be such that the ring will roll back and forth rather than sliding back and forth. This can be achieved by adjusting the diameter (dimension "D" in FIG. 3), the thickness (dimension "T" in FIG. 3) and the elasticity of the ring. The rolling of the ring occurs for the reason that, when the penis is moving relative to the wall 15 of the vagina (FIG. 2), this wall urges the outer circumference of the ring in one direction while the penis, acting through the condom, urges the inner circumference of the ring in the opposite direction. This causes the ring to roll along the penis.

The reciprocating motion of the elastic ring 21 during coitus not only applies a rubbing action to the genital organs of both the male and female but also applies a squeezing action to the penis to further stimulate the male partner.

Hash marks 24 indicate the point at which the attachment end 17 of the sheath 16 is attached to the condom. This attachment is made by applying a series of small droplets of rubber cement to the condom 11 at the location 24 and then rolling the distal end 17 of the sheath 17 into the cement to the position shown in FIG. 1. The rubber cement cures almost instantly and tightly bonds the attachment end 17 of the sheath 16 to the condom 11.

The series of small droplets of rubber cement, or a small continuous bead of rubber cement, will extend peripherally around the condom in a plane generally perpendicular to the axis of the condom. This firmly anchors the attachment end of the sheath to the condom.

Hash marks 27 indicate a second point at which the sheath 16 is attached or bonded to the condom 11. This second point is the point where the movement of the ring 21 relative to the condom 11 is stopped This is achieved by securing the sheath 17 to the condom 11 in the same manner that the attachment end 17 of the sheath is attached to the condom. A series of small droplets or a small bead of rubber cement extending around the condom at this point will securely bond the sheath 17 to the condom. To accomplish this bonding, the sheath would be placed on the condom and the ring 21 rolled to the left (FIG. 1) to a point between the point 27 and the distal end of the sheath 16 to leave the condom exposed at the point 27. The rubber cement would then be applied to the exposed condom at the point 27 and the ring then immediately rolled back to the right to cover the cement. The cement will cure almost instantly to securely bond the sheath to the condom at this point. Now, when the ring 21 is rolled to the left (FIGS. 1 and 2) it will roll until it reaches and is stopped by the bond at the point 27

While the sheath is shown here to be attached by an adhesive to the condom, it should be understood that other methods of attachment may be used. For example, instead of using cement at the point 24, the attachment end of the sheath may be provided with a rubber band or other elastic ring which snugly fits the penis to hold the sheath in place without the use of an adhesive. Likewise, the adhesive used at the point 27 may be omitted, using there instead a rubber band (encircling the sheath and condom) which has a sufficient width or snugness that it will not allow the ring 21 to roll past this point. However, the use of the adhesive is preferred.

FIGS. 1 and 2 illustrate the range of movement of the ring 21. From this, it can readily be seen that the ring 21 will roll back and forth, during coitus, between the positions shown in FIGS. 1 and 2 to further stimulate both the male and female partners. It can also be seen that as the ring 21 rolls to the left (FIG. 3) it is rolling up that part of the sheath extending between the stopping points of the ring so that this part of the sheath temporarily becomes a part of the ring.

Figure 3:
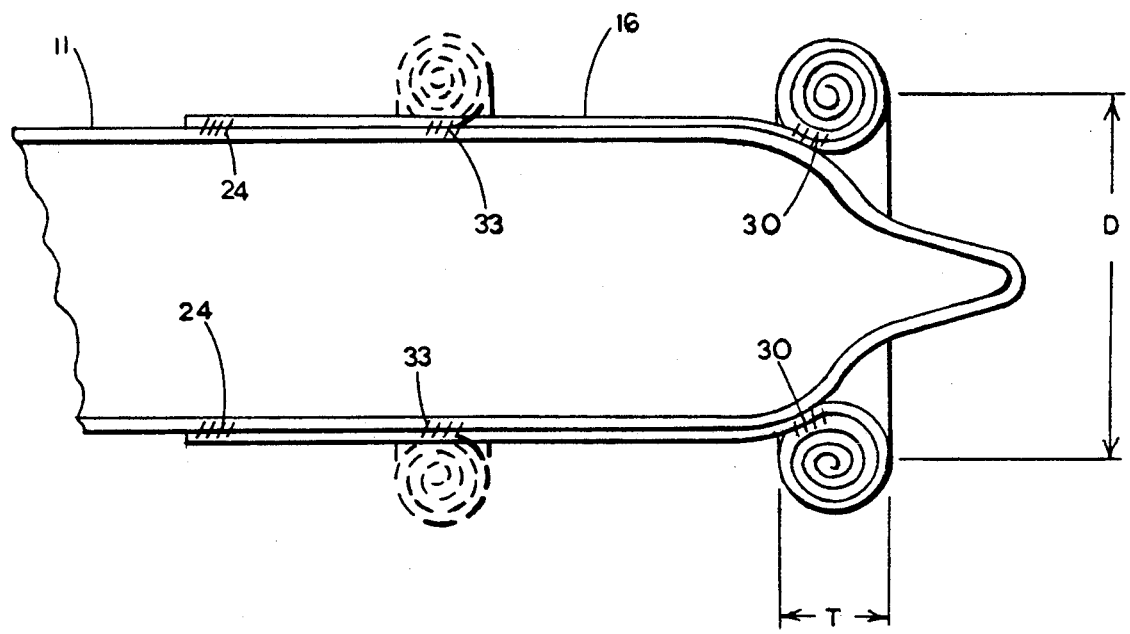
FIG. 3 is an enlarged fragmentary cross-sectional view showing a preferred embodiment of the invention.

FIG. 3 is an enlarged fragmentary view better illustrating how the distance of movement of the ring 21 is limited. In the embodiment shown, the ring 21 is made up by a length of the sheath which is rolled to form the ring. (It should be understood, of course, that the ring 21 may be a solid ring.) A small amount of rubber cement, applied as described above will lock the rolled ring 21 to prevent the ring itself from unrolling. This cement, represented by hash marks indicated by reference numeral 30 in FIG. 3, prevents further unrolling of the ring to the right (FIG. 3), thereby stopping it at the position shown in solid lines in FIG. 1. This is one end of the reciprocating range of the ring 21.

The position of the ring 21 at the other end of its range of movement is illustrated in dotted lines in FIG. 1. Rubber cement or some other adhesive, represented by hash marks 33 in FIG. 1, causes the ring to stop moving to the left (FIG. 3) relative to the condom when it reaches this point (shown in dotted lines in FIG. 3). The length of this range of movement can be adjusted by varying the position of the cement 33 along the condom 11. It should be noted that the cement 30 bonds the ring 21 to the sheath 16 to prevent unrolling of the ring while the cement 33 bonds the sheath 16 to the condom 11 to stop movement of the ring at this point.

Figure 4:
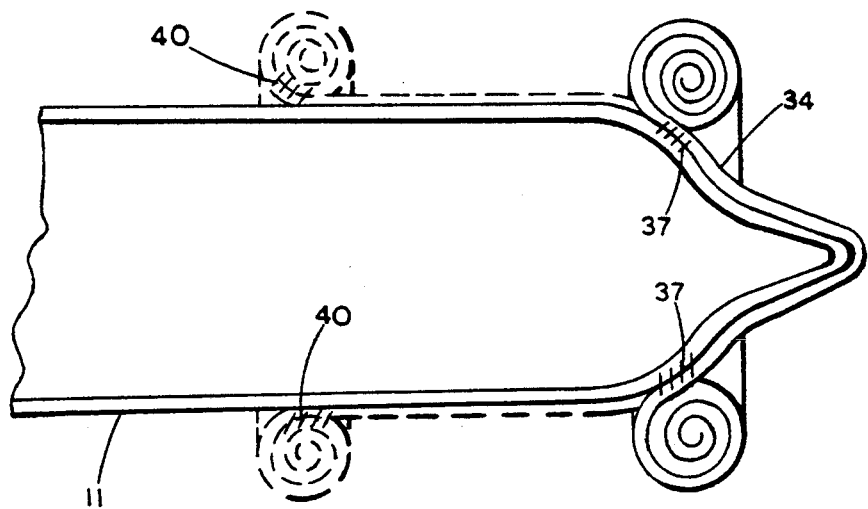
FIG. 4 is an enlarged fragmentary cross-sectional view showing a second embodiment of the invention.

FIG. 4 illustrates a second embodiment of the invention. In this embodiment the ring 21 is formed by rolling the open end of a second condom 34 which overlaps and is secured to the condom 11 by an adhesive represented by hash marks 37. This bond stops movement of the ring 21 to the right (FIG. 3) relative to the condom 11.

Dotted lines in FIG. 4 show the other limit of movement of the ring 21 in this embodiment. Cement represented by hash marks indicated by reference numeral 40 in FIG. 4 stops the ring 21 at this position.

It can be readily be seen that the ring 21 is free to roll back and forth along the end of the condom 11, and the user's penis, during coitus, thereby stimulating both the male and female partners. The ring 21 will also apply a squeezing action to the penis to further stimulate the male partner.

Figure 7:
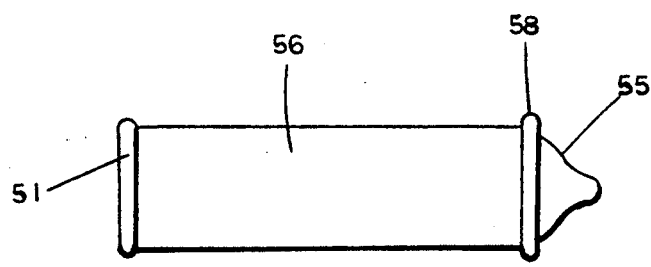
FIGS. 5, 6 and 7 are side views showing steps which may be used to make one embodiment of the invention.
Figure 6:
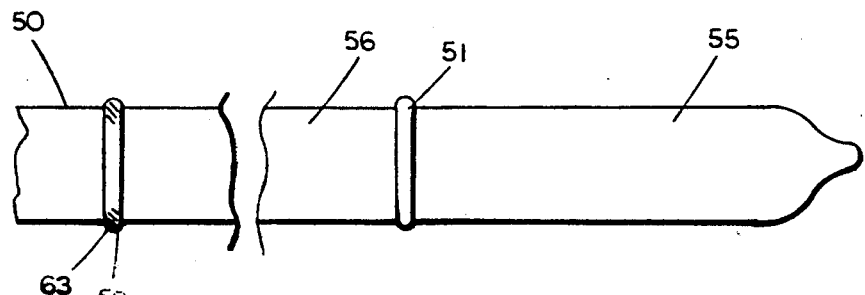
Figure 5:
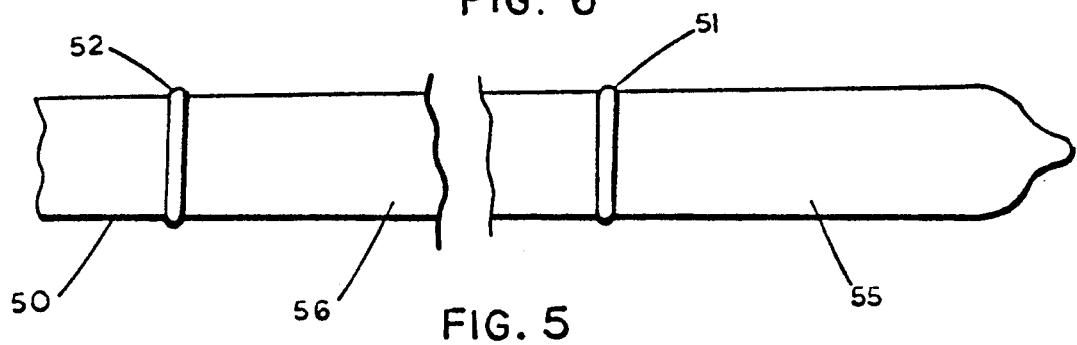

FIGS. 5–7 illustrate the steps in the process of making one embodiment of this invention. In this process the sheath is made as the condom is made and is an integral part of the condom.

In making condoms, a glass form is dipped one or more times in a latex solution and then withdrawn. This leaves the form coated with the latex solution which, when cured will be the condom. This same dipping and curing process is used in making the condom of this invention.

An elongated form 50 has mounted on it a pair of rubber rings 51 and 52. The ring 51 will be the ring that is now found at the open end of conventional condoms. The ring 52 will be the nucleus of a rolling ring to be later formed.

The form 50 is dipped one or more times in a latex solution, with the form being dipped to a sufficient depth that the latex solution covers the form from the ring 52 to the end of the form. The form is then withdrawn from the latex solution and the latex is cured in a known manner to form a condom 55 having its open connected to a sheath 56.

After curing, the upper end of the sheath 56 is rolled downward along the form 50 to form a rolling ring 58, as shown in FIG. 6. Before the ring 58 reaches the point where it is shown in FIG. 6, rubber cement, indicated by hash marks 63 in FIG. 5, is applied to the sheath at that point. When the ring is rolled into the rubber cement the cement cures almost instantly to prevent the ring from unrolling.

The dimension T of the ring 58 (FIG. 3) can be adjusted by varying the position of the ring 52 on the form. If the ring 52 is placed at a higher point on the form, for example, there will be more of the sheath to roll and the ring 58 will have a greater thickness, T, a smaller inner diameter and a larger outer diameter. Preferably, the inner diameter of the ring will be at least 5%, most preferably 10%, smaller than the diameter of the sheath. The inner diameter of the ring=D−T. The outer diameter=D+T.

The next step is to pull the sheath 56 down over the condom 55 so that it extends downward from the ring 51 and surrounds the condom 55. It can readily be seen that, if the ring 58 is to be properly positioned at the closed end of the condom 55, the distance from the ring 51 to the ring 58 (FIG. 6) should be about the same as the distance from the ring 51 to the closed end of the condom.

Figure 8:
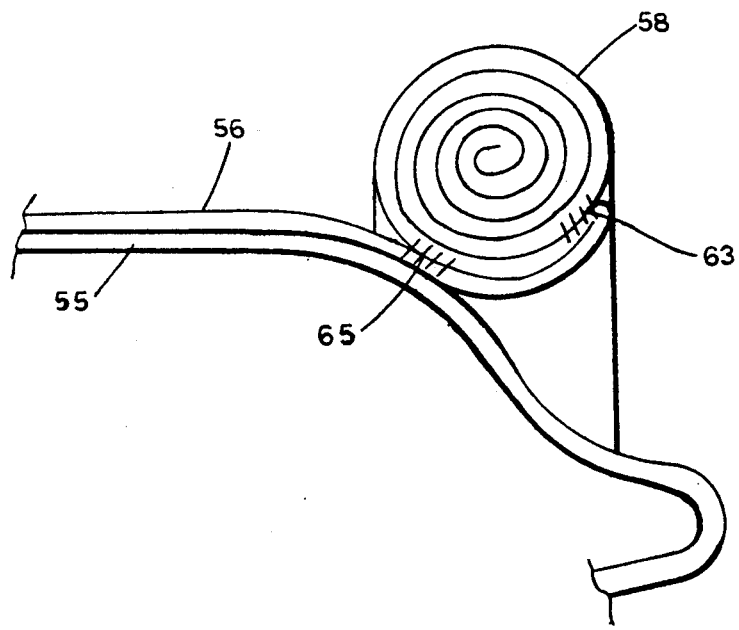
FIG. 8 is a greatly enlarged fragmentary view showing the preferred method of rolling the sheath of the device of FIGS. 5-7 to form the elastic ring.

It is preferred that the ring 58 be "retro-rolled" to complete the process of making the device. By "retro-rolled" it is meant that the ring is rolled at least part of a turn in the direction opposite the direction of rolling which was used to form the ring. This is clear from FIG. 8, where the major portion of the ring is rolled in one direction (down the form 50) and held in such rolled condition by the adhesive 63. The ring 58 is then rolled about ¼th or more turns in the opposite direction (up the form 50) and held in such retro-rolled configuration by cement represented by hash marks 65. The advantage of this is that all of the sheath which is not a part of the ring will be in contact with the condom, so that the ring is more likely to roll than to slide along the condom during coitus.

What is claimed is:

1. A contraceptive device, comprising
 a. a condom having the configuration of an elongated tube having an open end and a closed end,
 b. a sheath surrounding at least a portion of the tubular condom and having an attachment end and a distal end, said attachment end of said sheath being attached to the condom at a first point thereon, said distal end being located at a second point spaced from the first point, and c. an elastic ring secured to the distal end of the sheath, said sheath being unattached to the condom between said points such that the elastic ring is free to move back and forth between said points.

2. The contraceptive device of claim 1 wherein said point of attachment is spaced from the closed end of the condom and the ring attached to the distal end is adjacent to the closed end of the condom.

3. The contraceptive device of claim 2 wherein the inner diameter of the ring is at least 5% smaller than the diameter of the sheath.

4. The device of claim 2 wherein the inner diameter of the ring is at least 10% smaller than the diameter of the sheath.

5. The device of claim 2 wherein said first point of attachment is at a location on the sheath intermediate the attachment and distal ends of the sheath.

6. The device of claim 5 wherein the sheath is attached to the condom at two locations thereon, one of said locations being the end of said attachment end and the other location being at said intermediate point.

7. The device of claim 1 wherein the sheath is integral with the condom.

8. The device of claim 2 wherein the elastic ring is formed by rolling a portion of the sheath into a ring, said ring being secured against unrolling by an adhesive.

9. A contraceptive device, comprising a. a condom having a tubular configuration with an open end and a closed end, b. a tubular elastic sheath surrounding at least a portion of the condom and having an attachment end and a distal end, said attachment end being attached to the condom at a point spaced from the closed end of the condom, said distal end being positioned adjacent to said closed end, said sheath having a diameter at least 5% smaller than the diameter of the condom, and c. an elastic ring secured to the distal end of the sheath, said ring having an inner diameter no greater than 95% of the diameter of the sheath, said sheath being secured to the condom by rubber cement.

10. The device of claim 9 wherein the ring is a solid ring.

11. The device of claim 9 wherein the ring is formed by rolling a portion of the sheath.

* * * * *